United States Patent
Sandholm et al.

(10) Patent No.: US 10,939,887 B2
(45) Date of Patent: *Mar. 9, 2021

(54) SYSTEM AND METHOD OF ARTIFACT CORRECTION IN 3D IMAGING

(71) Applicant: PaloDEx Group Oy, Tuusula (FI)

(72) Inventors: Joonas Erik Sandholm, Helsinki (FI); Martti Kalke, Tuusula (FI)

(73) Assignee: PaloDEx Group Oy, Tuusula (FI)

( * ) Notice: Subject to any disclaimer, the term of this patent is extended or adjusted under 35 U.S.C. 154(b) by 611 days.

This patent is subject to a terminal disclaimer.

(21) Appl. No.: 15/418,121

(22) Filed: Jan. 27, 2017

(65) Prior Publication Data
US 2017/0135665 A1 May 18, 2017

Related U.S. Application Data

(63) Continuation of application No. 14/311,860, filed on Jun. 23, 2014, now Pat. No. 9,592,020.

(51) Int. Cl.
*A61B 6/00* (2006.01)
*A61B 6/14* (2006.01)
(Continued)

(52) U.S. Cl.
CPC ............ *A61B 6/5264* (2013.01); *A61B 6/032* (2013.01); *A61B 6/06* (2013.01); *A61B 6/14* (2013.01); *A61B 6/4085* (2013.01); *A61B 6/466* (2013.01); *A61B 6/469* (2013.01); *A61B 6/5217* (2013.01); *G06T 5/001* (2013.01); *G06T 7/0012* (2013.01); *G06T 7/11* (2017.01); *G06T 11/005* (2013.01); *G06T 19/20* (2013.01); *G06T 2207/10028* (2013.01); *G06T 2207/10116* (2013.01);
(Continued)

(58) Field of Classification Search
CPC .................................. A61B 6/14; A61B 6/032
See application file for complete search history.

(56) References Cited

U.S. PATENT DOCUMENTS 5,696,807 A * 12/1997 Hsieh ..................... A61B 6/032
378/109
7,526,060 B2 4/2009 Ziegler
(Continued)

FOREIGN PATENT DOCUMENTS

WO 2002086822 A1 10/2002
WO 2003009215 A1 1/2003
(Continued)

OTHER PUBLICATIONS

U.S. Appl. No. 11/577,041, filed Oct. 15, 2008.
(Continued)

*Primary Examiner* — Hoon K Song
(74) *Attorney, Agent, or Firm* — Andrus Intellectual Property Law, LLP

(57) ABSTRACT

A system and method of x-ray imaging includes obtaining a plurality of x-ray projection images of a patient. At least one object in the plurality of x-ray projection images is identified. A priori information of the identified at least one object is obtained. A three dimensional volume is reconstructed from the plurality of x-ray projection images. The a priori information is used to refine the acquisition of x-ray projection images or presentation of the three dimensional volume.

20 Claims, 5 Drawing Sheets

(51) Int. Cl.
*A61B 6/03* (2006.01)
*A61B 6/06* (2006.01)
*G06T 5/00* (2006.01)
*G06T 11/00* (2006.01)
*G06T 7/11* (2017.01)
*G06T 7/00* (2017.01)
*G06T 19/20* (2011.01)

(52) U.S. Cl.
CPC ............ *G06T 2207/30036* (2013.01); *G06T 2211/436* (2013.01)

(56) References Cited

U.S. PATENT DOCUMENTS

| | | | |
|---|---|---|---|
| 9,592,020 B2 * | 3/2017 | Sandholm | A61B 6/469 |
| 2009/0074278 A1 | 3/2009 | Beaulieu et al. | |
| 2014/0328450 A1 * | 11/2014 | Pal | G01N 23/046 378/5 |
| 2015/0029178 A1 * | 1/2015 | Claus | A61B 6/032 345/419 |

FOREIGN PATENT DOCUMENTS

| | | |
|---|---|---|
| WO | 2005076221 A1 | 8/2005 |
| WO | 2005076222 A1 | 8/2005 |
| WO | 2008065394 A1 | 6/2008 |
| WO | 2011055267 A1 | 5/2011 |
| WO | 2012056379 A1 | 5/2012 |

OTHER PUBLICATIONS

Liu et al., "Dynamic Bowtie for Fan-Beam CT", Journal of X-Ray Science and Technology, Jan. 1, 2013.
Shunhavanich et al., "Fluid-filled Dynamic Bowtie Filter: a Feasibility Study", pROC. of spie, Mar. 18, 2015, vol. 9412.
European Search Reported issued in Corresponding European Application No. 15 17 3359, dated Feb. 12, 2016.

* cited by examiner

SYSTEM AND METHOD OF ARTIFACT CORRECTION IN 3D IMAGING

CROSS REFERENCE TO RELATED APPLICATIONS

This application is a continuation of U.S. application Ser. No. 14/311,860 filed Jun. 23, 2014 which application published on Dec. 24, 2015 as U.S. 2015/0366525 in the English language, which application is incorporated herein by reference.

FIELD

The present disclosure relates to x-ray imaging systems and methods. More specifically, the present disclosure relates to the use of a priori information to address artifacts in 3D imaging.

BACKGROUND

U.S. Pat. No. 7,526,060 discloses that the reconstruction of images of an object of interest may introduce artifacts along lines of high gradients of absorption values. These artifacts may be removed by a statistical weighing during reconstruction of the image.

U.S. patent application Ser. No. 11/577,041 discloses a method for reducing artifacts in an original computed tomography (CT) image of a subject produced from original sinogram data. In the method an artifact creating object is re-projected in the original sinogram data to produce modified sinogram data in which missing projection data is absent. Replacement data for the missing projection data is interpolated and replaces the missing projection data in the original sinogram data. A final CT image is reconstructed using the final sinogram data to obtain an artifact-reduced CT image.

International Patent Application Publication No. WO 2012/056379 discloses a method that includes displaying at least one of projection data or reconstructed image data having visually observable artifacts. One or more sample images having artifacts similar to the visually observable artifacts are identified. Information about the identified one or more of the sample images is displayed.

International Patent Application Publication No. WO 2008/065394 discloses a method and apparatus for reducing artifacts caused by a metal implant, thorax/pelvic streaking, and lower dose streaking in reconstruction images. An initial reconstruction of the object using an iterative process is performed and an ideal correspondence of the implant is generated. A region affected by the implant is located and inconsistencies caused by the implant inside a scanned object are detected and analyzed. The initial reconstruction the real correspondence of the implant is approximated and the initial reconstruction is updated. The approximated correspondence of the implant is isolated and the implant-free reconstruction in the location of the implant synthesized.

International Patent Application Publication No. WO 2005/076221 discloses a reconstruction processor that reconstructs acquired projection data into an uncorrected reconstructed image. A classifying algorithm classifies pixels of the uncorrected reconstruction image at least into metal, bone, tissue, and air pixel classes. A pixel replacement algorithm replaces metal class pixels of the uncorrected reconstruction image with pixel values of the bone density class to generate a metal free image. A morphological algorithm applies prior knowledge of the subject's anatomy to the metal free image to correct the shapes of the class regions to generate a model tomogram image. A forward projector forward projects the model tomogram image to generate model projection data. A corrupted rays identifying algorithm identifies the rays in the original projection data which lie through the regions containing metal objects. A corrupted rays replacement algorithm replaces the corrupted regions with corresponding regions of the model projection data to generate corrected projection data. The reconstruction processor reconstructs the corrected projection data into a corrected reconstructed 3D image.

International Patent Application Publication No. WO 2005/076222 discloses the correction of artifacts caused by high attenuating objects. Artifact correction is provided in reconstructed images by correcting beam-hardening artifacts caused by high attenuating objects on the basis of a physical correction method, which uses the data in the shadow of the high attenuating objects without disregarding any physical information. The noise of line integral through high attenuating objects is reduced by using adaptively filtered projections.

International Patent Application Publication No. WO 2003/009215 discloses a system and method for reducing streak artifacts and eliminating inhomogeneity in CT imaging by correcting elimination and using adaptive three-dimensional filtering. A direction of streak artifacts and a degree of inhomogeneous densities are estimated by gray scale morphology dilation.

International Patent Application Publication No. WO 2002/086822 discloses a method for artifact reduction in CT imagines that includes reconstructing a first data imaging using an inexact reconstruction algorithm. The first data image is segmented to provide a second image with high attenuation objects separated from low attenuation objects. The second image is re-projected to form a second set of data and a third image is reconstructed from the second data set using an inexact reconstruction algorithm. At least those portions of the third image outside of the high attenuation object are subtracted from the first image.

BRIEF DISCLOSURE

An exemplary embodiment of a method of x-ray imaging includes obtaining a first plurality of x-ray projection images of a patient. At least one object is identified in the first plurality of x-ray projection images. A priori information of the at least one identified object is obtained. A three dimensional (3D) volume is reconstructed from the second plurality of x-ray projection images and a priori information of the at least one identified object to produce a reconstructed 3D image.

An additional exemplary embodiment of a method of x-ray imaging includes obtaining a first plurality of x-ray projection images of the patient. At least one object is identified in the first plurality of x-ray projection images. A priori information of the at least one identified object is obtained. A region of interest (ROI) is automatically located in the first plurality of x-ray projection images based upon the at least one identified object and the a priori information. Beam dimensions are calculated for a second plurality of x-ray projection images from the ROI. An x-ray radiation source is collimated to narrow an emitted x-ray radiation beam to the calculated beam dimensions. An intensity of the x-rays emitted from the x-ray radiation source is adjusted based upon the a priori information. The emitted x-ray radiation beam is dynamically filtered to attenuate a portion of the emitted x-ray radiation beam that is out of alignment with the at least one identified artifact causing object. A second plurality of x-ray projection images are obtained with the emitted x-ray radiation beam. A three dimensional (3D) volume is reconstructed from the second plurality of x-ray projection images to produce a reconstructed 3D image.

An exemplary embodiment of a system for x-ray imaging includes a x-ray emitter configured to emit an x-ray beam. A collimator is operable to restrict dimensions of the x-ray beam to achieve a field of view (FOV) in a subsequent 3D reconstruction. An x-ray receiver is configured to receive the x-ray beam to create projection images. A processor received a first plurality of projection images from the x-ray receiver. The processor obtains an identification of at least one object within the plurality of projection images. The processor obtains a position of the at least one object and operates the collimator to adjust the dimensions of the x-ray beam based at least in part upon the obtained position of the at least one object. The processor further receives a second plurality of projection images from the x-ray receiver. The processor reconstructs a three dimensional (3D) volume from the plurality of x-ray projection images and the position of the identified at least one object and produce a reconstructed 3D image from the 3D volume. A graphical display is configured to present the reconstructed 3D image.

DETAILED DISCLOSURE

In the present description, certain terms have been used for brevity, clearness and understanding. No unnecessary limitations are to be implied therefrom beyond the requirement of the prior art because such terms are used for descriptive purposes only and are intended to be broadly construed. The different systems and methods described herein may be used alone or in combination with other systems and methods. Various equivalents, alternatives and modifications are possible within the scope of the appended claims. Each limitation in the appended claims is intended to invoke interpretation under 35 U.S.C. § 112(f) only if the terms "means for" or "step for" are explicitly recited in the respective limitation.

Figure 1:
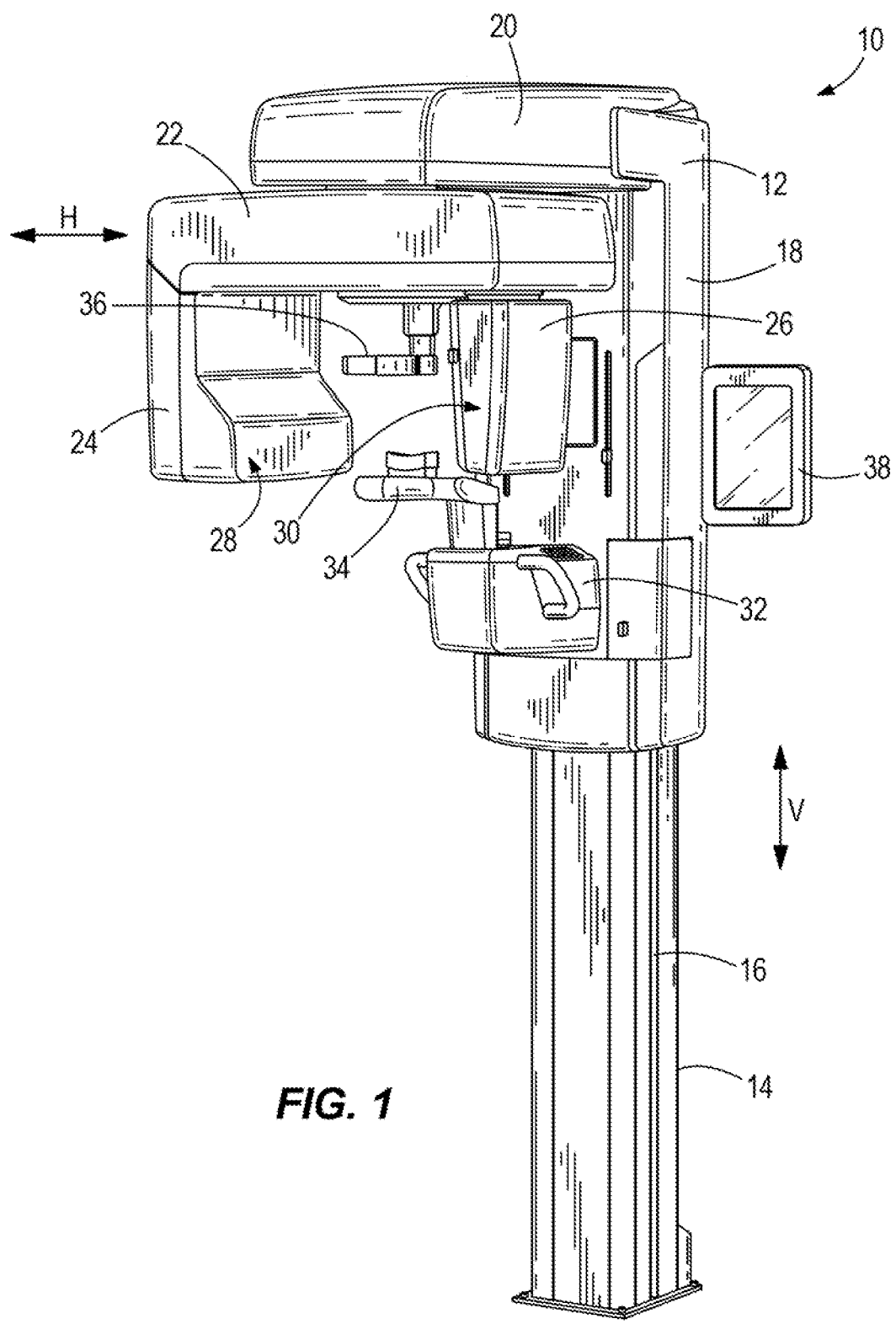
FIG. 1 is a perspective view of an exemplary x-ray imaging apparatus.

FIG. 1 depicts an exemplary embodiment of an x-ray imaging apparatus for acquiring x-ray images of an object, exemplarily a dental or medical patient. While x-ray imaging is exemplarily used herein, it is understood that additional embodiments may be implemented in other image modalities. In the particular example shown, the imaging apparatus 10 is configured for three-dimensional (3D) imaging of the dentomaxillofacial complex of the human skull; however, other configurations of apparatuses for imaging of other portions of a patient's anatomy can instead be employed with the concept of the present disclosure. The x-ray imaging apparatus 10 can optionally be configured to conduct different types of imaging procedures, including, but not limited or panoramic imaging (standard, pediatric, orthozone, wide arch, orthogonal and/or the like), cephalomatric imaging (cephalo pediatric lateral projection, cephalo lateral projection, cephalo postero-anterior, and/or the like), and/or 3D imaging. FIG. 1 depicts just one example of an x-ray imaging apparatus for use with the concepts in the present disclosure. Other examples of x-ray imaging apparatus can be instead be employed, including, but not limited to computed tomography (CT) and fluoroscopic imaging The imaging apparatus 10 includes a housing 12 that is moveably supported on a support column 14. The housing 12 can be moved up and down in the vertical direction V via a conventional guide motor (not shown) that is configured to move the housing 12 vertically up and down along a track 16 extending along the support column 14. The housing 12 includes a generally vertically extending guide section 18 disposed on the support column 14 and a generally horizontally extending support section 20 extending generally horizontally from the guide section 18. The support section 20 supports a rotating section 22, which is rotatable in a horizontal plane H with respect to the stationary support section 20. The support section 20 and/or rotating section 22 may contain a conventional guide motor (not shown) configured to rotate the rotating section 22. In an another exemplary embodiment, the imaging apparatus 10 can be mounted to a support structure (not depicted) exemplarily a wall instead of or in addition to being supported by the column 14.

An x-ray emitter housing 24 and an x-ray receiver housing 26 are opposed from each other and extend generally vertically from the rotating section 22. The emitter housing 24 contains an x-ray emitter generally located at 28, although not depicted, and supported in the emitter housing 24. The x-ray emitter is positioned to emit x-rays from the x-ray emitter through the object being imaged (e.g. the patient) to an x-ray receiver generally located at 30, although not depicted, supported in the x-ray receiver housing 26. A patient positioning housing 32 extends from the guide section 18 and includes a chin support 34 for positioning the head of the patient (not depicted) between the opposed x-ray emitter 28 and the x-ray receiver 30. A head support 36 extends from the horizontal support section 20 through the rotating section 22. The chin support 34 and the head support 36 may be optional, and positioning of the patient may be carried out in other manners.

In operation, the x-ray emitter projects a beam (not depicted) of x-rays in the direction of the x-ray receiver. The x-rays pass through a portion of the patient's anatomy (e.g. patient's head). The anatomical structures through which the x-rays pass absorb varying amounts of the x-ray energy. After passing through the patient, the attenuated x-rays are absorbed at the x-ray receiver which converts the magnitude of the received x-ray energy and produces a digitized output representative of the unabsorbed x-rays at the x-ray receiver. The collection of digitized outputs from the x-ray receiver that correspond to a single emission of a beam of x-rays from the x-ray emitter may be referred to a projection image of the object being imaged, exemplarily the patient's head.

In accordance with the embodiment described above and shown in FIG. 1, as well as other similar embodiments, the x-ray emitter and x-ray receiver are held in correspondence to one another by the rotating section 22. The rotating section 22 is rotated exemplarily by a guide motor. The rotation of the rotating section 22 moves the x-ray emitter and the x-ray receiver about the object to be imaged, exemplarily about a rotation axis. In an embodiment, the rotation axis is oriented with the center of the object to be imaged. In an additional embodiment, the rotation axis may be aligned with a particular anatomical feature of interest within the patient's head. Other techniques or alignments for the rotation axis may also be used as will be recognized by a person or ordinary skill in the art. As the x-ray emitter and x-ray receiver are rotated about the patient's head, the imaging apparatus 10 operates to acquire a plurality of projection images of the patients head taken at incremental angles of rotation. In a non-limiting embodiment, projection images are acquired at 1° increments about a 180° or 3600 rotation. As merely exemplary disclosure, embodiments may capture between 250-1200 projection images in an imaging operation; however, this is not intended to be limiting on the present disclosure. Such increments may represent fractions of a degree of rotation. Other angular increments and other total angles of rotation are contemplated within the scope of the disclosure.

Figure 2:
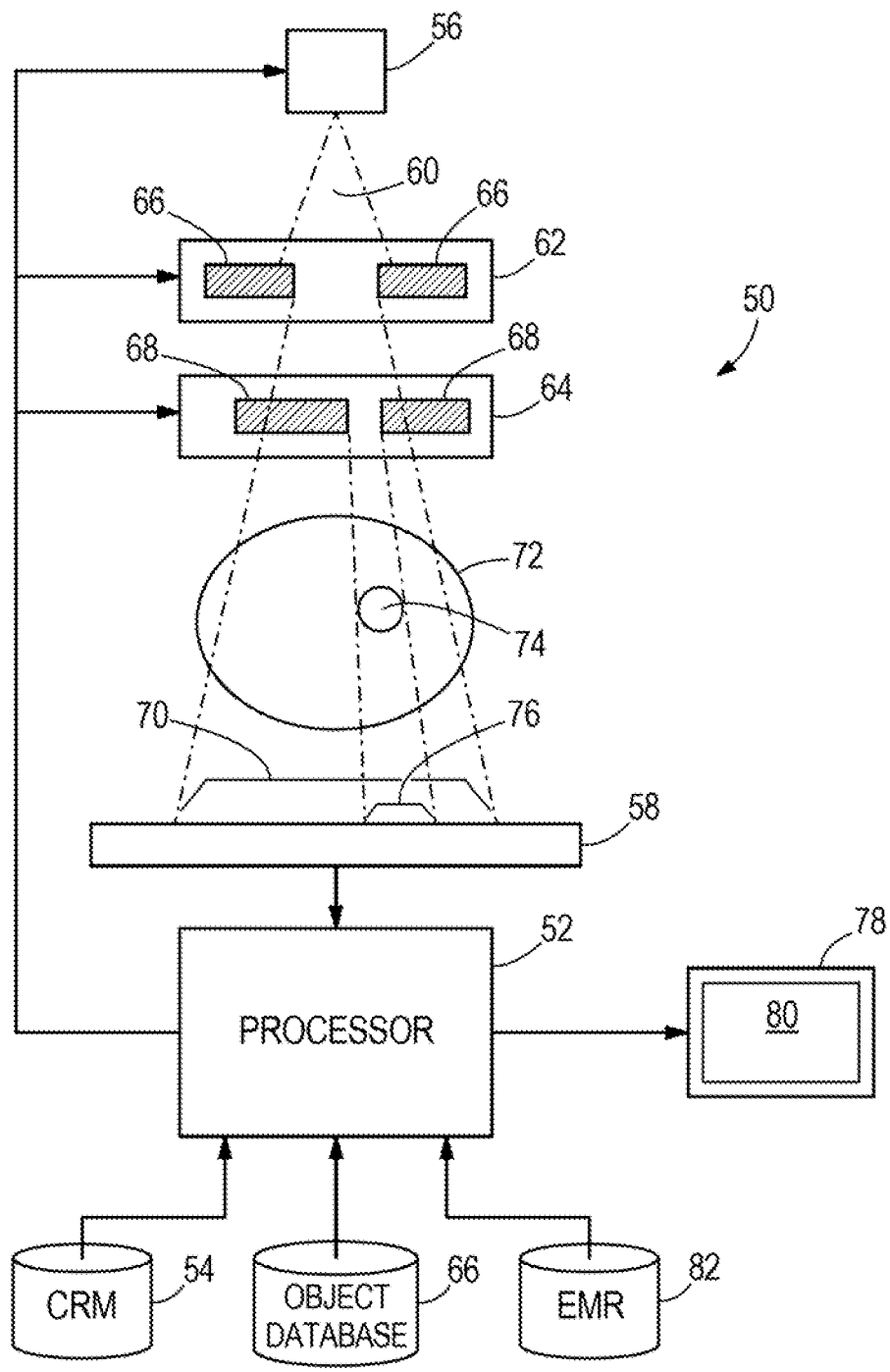
FIG. 2 is a schematic representation of an exemplary embodiment of an x-ray imaging system.

FIG. 2 depicts an exemplary embodiment of a system for x-ray imaging 50. The system 50 includes a processor 52 and a computer readable medium 54 that is programmed with computer readable code that upon execution by the processor 52 causes the processor 52 to perform the operations and functions as disclosed herein. While the processor 52 is depicted as a component separate from the computer readable medium 54, it is understood that in some embodiments, the computer readable medium 54 may be incorporated as part of the processor 52 while remaining within the scope of the present disclosure. Although the embodiment of the x-ray imaging system 50 depicted in FIG. 2 depicts a single processor 52, it will be recognized that in additional embodiments, two or more processors may be used in coordination to function together to carry out the functions and operations as described herein. Therefore, references to the processor as found herein should be interpreted to include such multiple processor systems.

The processor 52 is communicatively connected to an x-ray emitter 56 and an x-ray receiver 58 as described above with respect to FIG. 1, without being depicted therein. The x-ray emitter 56 projects a beam 60 of x-rays from the x-ray emitter 56 in the direction of the x-ray receiver 58. In one embodiment described in greater detail herein the processor 52 operates the x-ray emitter 56 to control an intensity of the beam 60 emitted from the x-ray emitter 56. In an exemplary embodiment, the beam 60 is a cone beam, although it will be recognized that alternative embodiments by use other beam shapes, including, but not limited to, fan beams or line beams as may be recognized by one of ordinary skill in the art.

As will be described in further detail herein, the processor 52 is further communicatively connected to a collimator 62 and a filter 64. The collimator 62 and the filter 64 are respectively operable by the processor 52 to move collimator leaves 66 and filter leaves 68 in order to shape and/or partially attenuate the beam 60 of x-rays emitted from the x-ray emitter 56. In an embodiment, the collimator 62 is operated to place the collimator leaves 66 in the path of the beam 60, such as to define dimensions of the beam of x-rays. The dimensions of the beam of x-rays are exemplarily shown herein by beam width 70, although it will be appreciated that the dimensions of the beam of x-rays may also be defined in a height or vertical dimension. This may exemplarily also be controlled by the collimator 62. As used herein, the field of view (FOV) is a size of the extent of the volume to be imaged. In embodiments, the FOV is reconstructed in three dimensions from the plurality of projection images as disclosed in further detail herein. FOV may exemplarily be defined as a height and diameter of a cylinder. The FOV can be limited by the imaging geometries, for example the spatial location of the x-ray source and detector corners related to each projection image, including the size of the detector, the distance from the x-ray source to the object, and the distance from the object to the detector. In an embodiment, the dimensions of the beam of x-rays may be selected based upon a determined or desired FOV in a subsequent 3D reconstruction. As further used herein, a region of interest (ROI) is of a two-dimensional projection image is a region inside of the two-dimensional projection image that includes the clinically relevant information. In the exemplary embodiment of FIG. 2, the ROI may exemplarily be a region in a projection image (not depicted) that includes the image of the artifact causing object 74 and some additional extent around the object. In an additional embodiment, the dimensions of the beam of x-rays may be adjusted to an object to be imaged 72, which can be, for example, a portion of a patient's head or other body part. In a still further additional embodiment, the dimensions of the beam of x-rays may be adjusted to approximate (without being smaller than) the ROI of the object to be imaged 72. This limits radiation exposure to portions of the object 72 that are not of interest to the purpose of the imaging.

Similarly, the filter 64 is operated such that at least one filter leaf 68 impinges on the FOV of the beam 60 of x-rays. The at least one filter leaf 68 is configured to only attenuate the x-rays of the beam 60 in a portion of the beam 60 to a determined reduced level, while allowing a portion 76 of the beam 60 to pass through the filter 64 at the full strength. In an exemplary embodiment as disclosed in further detail herein, the filter 64 may be operated such that the at least one filter leaf 68 attenuates the portions of the beam 60 that are not in alignment with an identified artifact causing object 74 located within the region of interest 70. This leaves a full intensity portion 76 of the x-ray beam to be directed at the artifact-causing object 74. In a non-limiting embodiment, the stronger x-rays impinging on the artifact-causing object 74 can mitigate the artifacts caused by the object 74, while the attenuation of the other parts of the beam 60 by filter 64 serves to reduce the total x-ray energy to which the object 72 is exposed.

As described above, the x-ray receiver 58 operates to receive the attenuated x-rays after they have passed through the object 72 to be imaged, for example, the patient's head. The received x-rays are converted by the x-ray receiver 58 to a digitized representation of a projection image of the object 72 and/or an ROI of the object 72. The digitized representation of the projection image is provided to the processor 52. In an exemplary operation, a plurality of projection images of the object at incremental angles about the object 72 are provided to the processor 52 from the x-ray receiver 58 in a single imaging session.

The inventors have observed that objects of foreign nature can cause imaging artifacts in reconstructed volumes from the received projection images due to high radiopacity of the foreign objects in comparison to the surrounding anatomical structures. For example, high radiopacity can cause phenomena such as photon starvation, photon scattering, and beam hardening—each of which may be observed as artifacts in a reconstructed 3D volume. These artifact-causing objects can be, for example, dental implants, abutments, metal copings, frameworks, or other dental appliances. The artifact-causing objects may, for example, be made of metal; however, such objects may also be constructed of ceramic or other material of high radiopacity. Still further examples of artifact causing objects may include dentomaxillofacial prosthetics or orthodontic treatment appliances.

In an embodiment, the processor 52 executes computer readable code, exemplarily from the computer readable medium 54, such that the processor 52 identifies at least one artifact-causing object in one or more of the received projection images. Such identification may exemplarily be performed using pattern matching or other object identification algorithms and may be carried out on either one or more of the received projection images, or may be identified from other scout or procedure planning images acquired in embodiments by the x-ray receiver prior to the acquisition of the projection images.

The processor 52 may further analyze the projection images or scout images to identify a position, location, or orientation of the identified object within the region of interest imaged by the projection images. In a still further embodiment, the processor analyzes the projection images or scout images to further determine a size, shape, and/or Houndsfield Unit (HU) value of the object. In such an embodiment by identifying the artifact-causing object, identifying the position of the object and obtaining at least one of the physical properties of the identified object, namely an object size and/or shape, the processor can operate to reconstruct an initial 3D volume from the projection images that includes the artifact-causing object as a known volume of a particular shape, size, position, and radiological density within the region of interest being reconstructed in three dimensions. In a non-limiting embodiment, the processor 52 may exemplarily use an algebraic reconstruction technique (ART) or a filtered back projection (FBP) to create the initial 3D volume from the projection images with the model artifact-causing object. The processor may then continue the reconstruction in an iterative process to refine the 3D volume to produce a reconstructed 3D image.

The processor 52 may be communicatively connected to a graphical display 78 that is operable by the processor 52 to visually present the reconstructed 3D image. In some embodiments, the graphical display 78 may be a flat screen display while in still further embodiments, the graphical display 78 may also be a touch-sensitive graphical display such that the graphical display 78 also operates as an input device. While in alternative embodiments a separate input device, for example a keyboard or a mouse (not depicted), may be connected to the processor 52 such that the user may input data values or commands as will be described in further detail herein.

In an alternative embodiment, the processor 52 identifies at least one artifact-causing object in at least one of the projection images or a scout image and this identification is used by the processor 52 to access an object database 66 on a computer readable medium that stores a plurality of physical properties each associated with a known artifact causing object, exemplarily a dental implant or appliance. The physical properties stored in the object database 66, may include, but are not limited to: shapes, sizes, or dimensions of potentially identified objects. The object database 66 may also include radiopacity of each of the objects in the database. This information may be, for example, acquired from the object manufacturer, from third party testing, manufacturer or material information sheets, or CAD/CAM software for custom designed objects. In alternative embodiments, an industrial CT may be used to acquire radiopacity of material of each object. In a still further embodiment, a data table of known material radiopacity is used. However, a person of ordinary skill in the art will recognize other sources of such physical properties to be associated with identified objects.

Figure 4A:
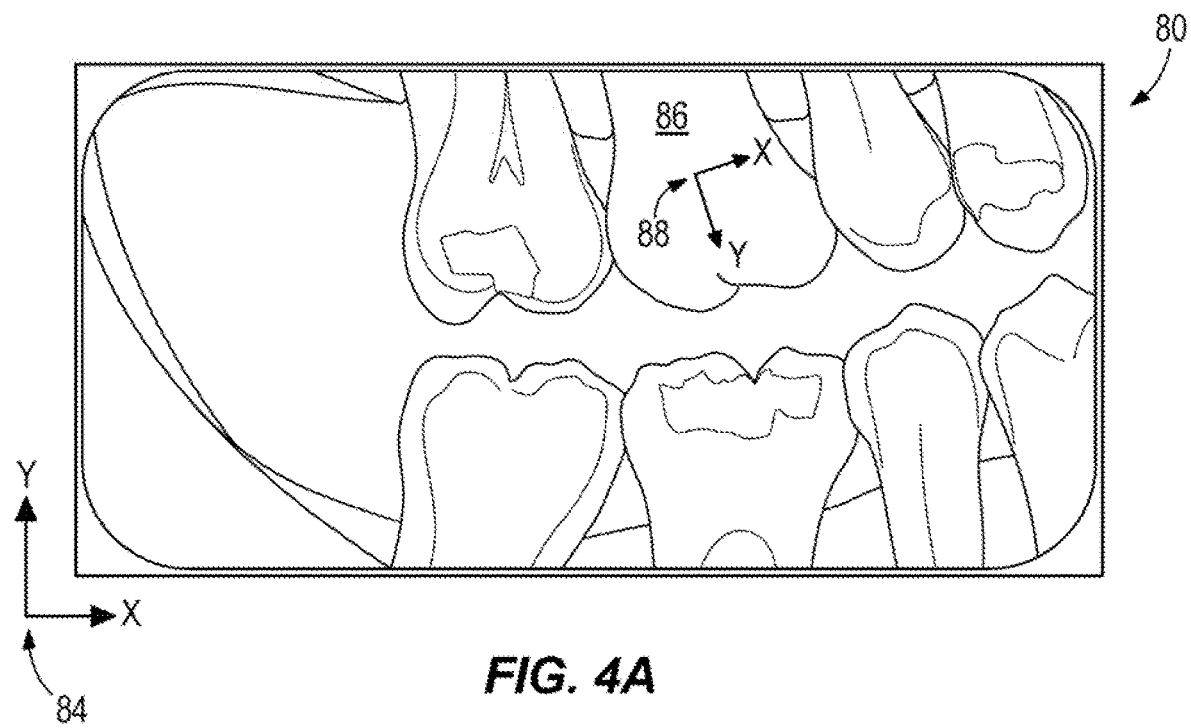
FIGS. 4A and 4B depict exemplary embodiments of graphical presentation of x-ray images.
Figure 4B:
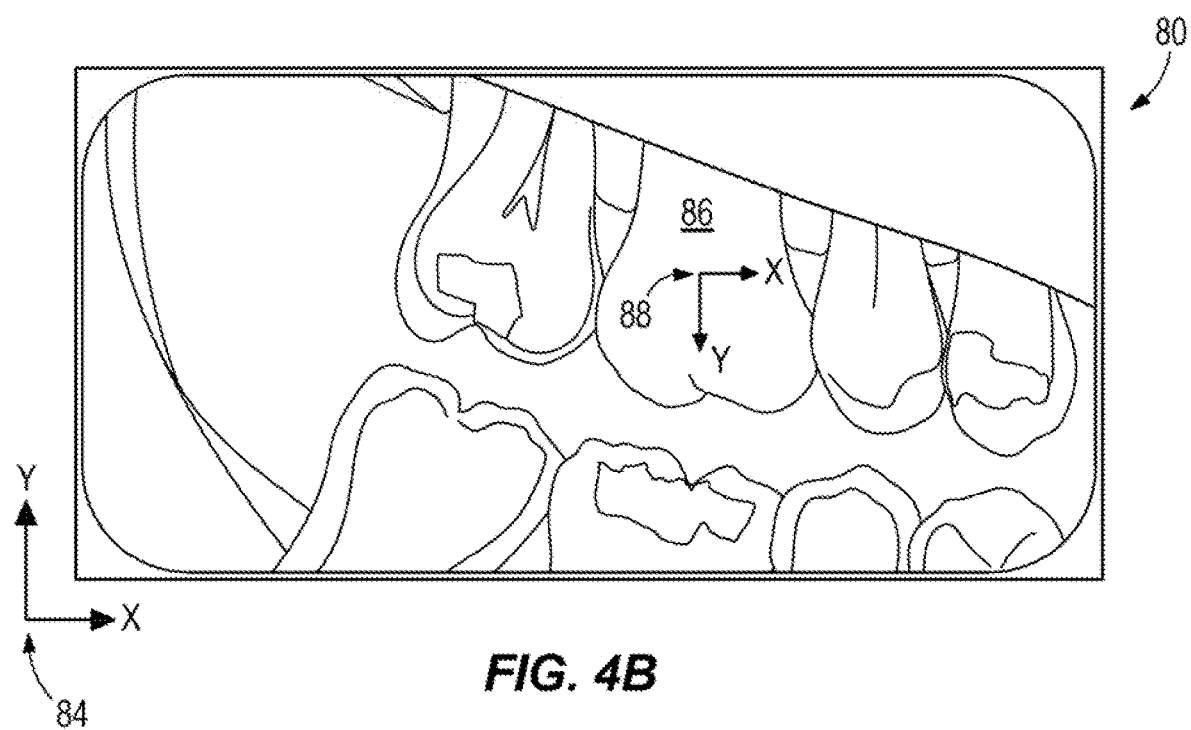

In an exemplary embodiment, the processor 52 uses the obtained a priori information of at least one physical property of the artifact causing object to establish a coordinate system comprising a plurality of axes for the identified at least one artifact causing object. In an embodiment, the graphical display 78 presents the reconstructed 3D image in a graphical user interface (GUI) 80. FIGS. 4A and 4B depict exemplary embodiments of reconstructed x-ray images as may be presented on GUI 80. While the images depicted on the GUI 80 in FIGS. 4A and 4B are two dimensional (2D) x-ray images, it is understood that these two dimensional x-ray images may either be two dimensional projection images, or in additional embodiments may be 2D slices of a reconstructed 3D volume. In still further embodiments, the GUI 80 may present the reconstructed 3D image. As stated above, the GUI 80 may have a coordinate system with a plurality of axes, exemplarily indicated at 84. Similarly, the identified artifact causing object 86 has a defined coordinate system of a plurality of axes indicated by 88. As stated above, the coordinate system 88, may be determined from the a priori information of the identified at least one artifact causing object which may be physical properties of such artifact causing objects, including a physical orientation thereof. In an exemplary embodiment, the presentation of the x-ray projection image, 2D slice of reconstructed 3D volume, or reconstructed 3D image may be transformed, for example, by rotation and/or translation, within the GUI 80 such that the coordinate system 84 of the GUI 80 and the coordinate system 88 of the artifact causing object 86 are aligned in at least one of the coordinate axes. Exemplarily, FIG. 4A represents the original image and FIG. 4B represents the image rotated such that the x axis of the GUI coordinate system 84 and the artifact causing object coordinate system 88 are in alignment. This can facilitate review of the medical images by a clinician by establishing a frame of reference between the orientation of the GUI and the orientation of the known artifact causing object within the region of interest of the patient.

In another exemplary embodiment, the processor 52 is further communicatively connected to a patient electronic medical record 82 stored on a computer readable medium. In an embodiment, the patient electronic medical record 82 may be stored in a database of electronic medical records for a plurality of patients. The electronic medical record 82 may provide the processor 52 with an identification of any known artifact-causing objects within the region of interest to be reconstructed by the processor, while in still further embodiments, the electronic medical record may further include a modeled position of the object with respect to other anatomical features of the patient. In such an embodiment, the processor 52 would not be required to derive an object position or location within the region of interest.

In still further exemplary embodiments, as described above, the system 50 may first acquire at least one or two scout projection images, and a known artifact causing object is identified in the scout images. In embodiments, the use of additional a priori information regarding the artifact causing object can facilitate in the detection and precisely locating the artifact causing object within the plurality of projection imaging. In one non-limiting embodiment, the use of the additional a priori information regarding the artifact causing object, exemplarily a location, or a physical property of the known artifact causing object and this additional information can facilitate the identification of the artifact causing object in the projection images, particularly if the artifact causing object has a radiopacity, exemplarily in Houndsfield units (HU) similar to that of the surrounding tissue, bone, or tooth.

In another exemplary embodiment, with improved identification of the location, position, and shape of the artifact causing object in the first plurality of images obtained as scout images and in a subsequent plurality of projection images used for obtaining the medical images, the processor 52 can identify if the patient has moved between the acquisition of the first plurality and second plurality projection images, or within a series of projection images. This identification can result in an indication that the movement of the patient may have resulted in a motion artifact. Alternatively, a 3D reconstruction from the acquired projection images can be modified such as to account for the identified motion artifact. In a still further embodiment, incongruities between the locations of the known artifact causing object within projection images may result in an identification of a misalignment or mis-calibration of the imaging system 50, exemplarily, but not limited to, a mis-identification or mis-calibration of the rotation center or rotation profile of the emitter 56 and the detector 58.

Figure 3A:
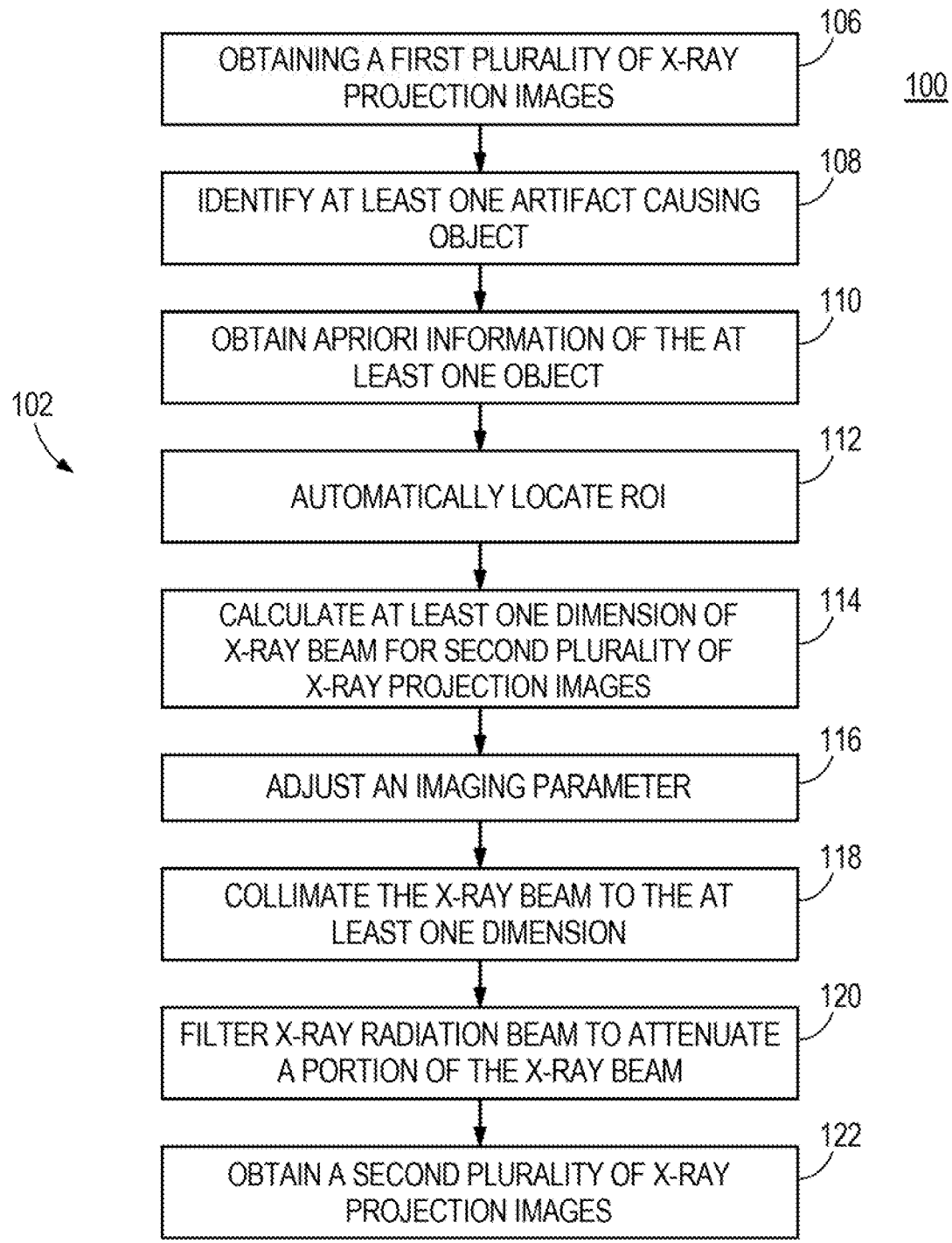
FIG. 3A is a flow chart that depicts an exemplary embodiment of a method of x-ray image acquisition.
Figure 3B:
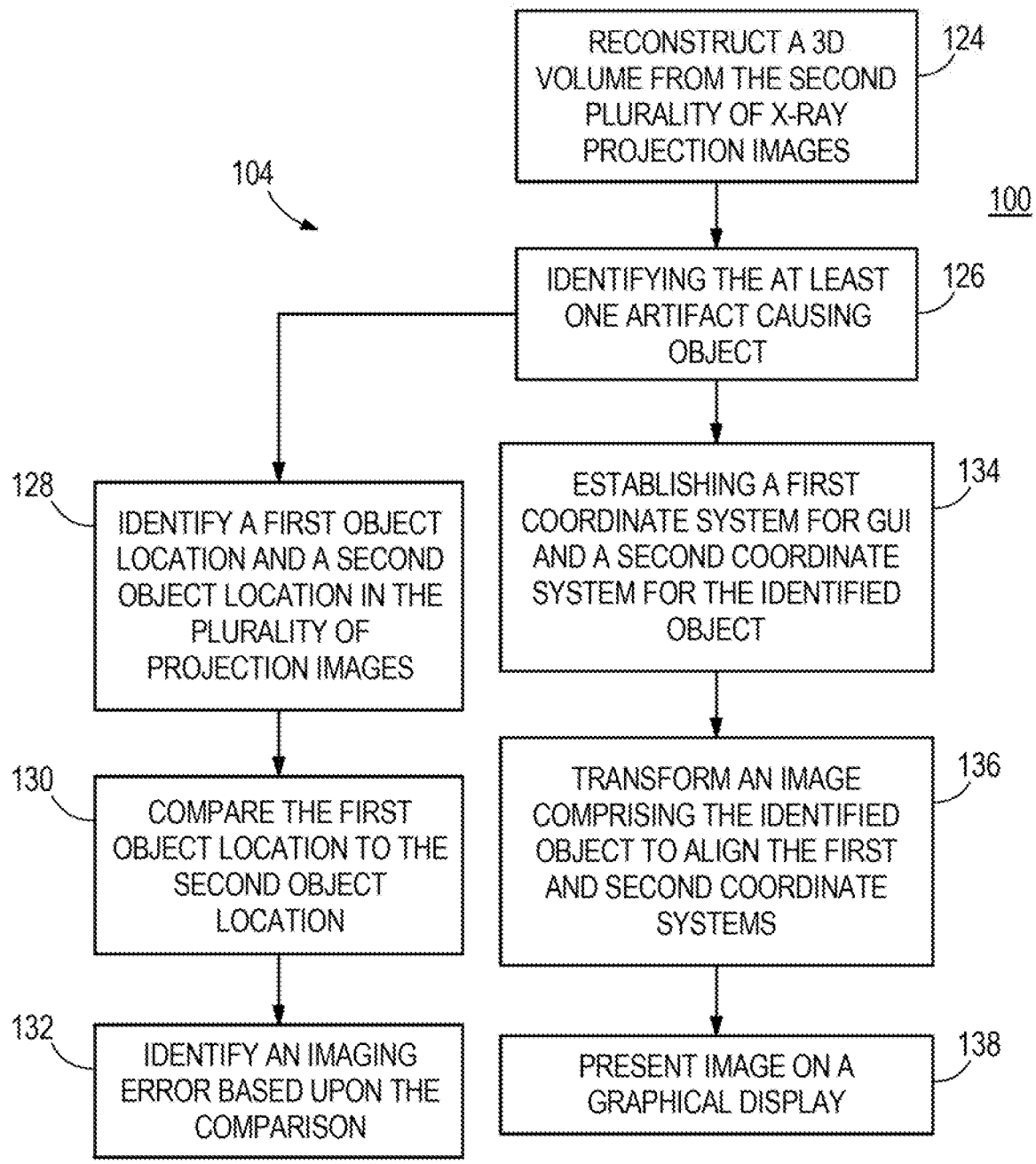
FIG. 3B is a flowchart that depicts an exemplary embodiment of a method of presentation of x-ray images.

FIGS. 3A and 3B are flowcharts that depict an exemplary embedment of a method of x-ray imaging 100. It is to be recognized that embodiments of the method 100 may be carried out without each of the steps as disclosed herein or in conjunction with additional steps. Still other embodiments may conduct operations as disclosed here in alternative orders while remaining within the scope of the present disclosure. The method 100 may exemplarily be performed as a sub method of image acquisition 102 depicted in FIG. 3A, and a sub method of image presentation 104, depicted in FIG. 3B, while other embodiments may only carry out functions of one or the other sub methods 102, 104. At 106 a first plurality of x-ray projection images are obtained. The x-ray projection images may be obtained by rotating an x-ray emitter and an x-ray receiver about the head of a patient and obtaining a series of projection images at incrementally varying angles about the patients head. The first plurality of projection images may be two or more scouting or planning images which may be used for calibration and imaging procedure set up. The scouting or planning images can, for example, use a lower x-ray intensity than that used for the subsequent images that will be processed for the 3D reconstruction. In an exemplary embodiment, the first plurality is two scouting images.

At 108 at least one object is identified in the first plurality of projection images. In an exemplary embodiment, the object is an artifact-causing object such as a dental implant. The object may be identified by a processor operating image processing programs or algorithms on one or more of the first plurality of x-ray projection images. In alternative embodiments, a user input is received that identifies at least one object in the region of interest that is imaged in the first plurality of projection images. While in still further embodiments, the object is identified in an input from an electronic medical record of the patient.

At 110 a priori information of the identified object is obtained. Exemplarily, a priori information may be a position or location of the object within the region of interest. In an embodiment, a detailed relative position of the object may be stored in the patient's electric medical record and this information may be accessed by a processor. In a still further embodiment, the a priori information is at least one physical property of the identified object.

Exemplary physical properties may include, but are not limited to, the dimensions, size, and/or shape of the object. The at least one physical property may also include a radiopacity of the object, a radiolucency, or Houndsfield units of the object. This information can be determined before the object (exemplarily a dental implant) is placed in the patient, for example by 3D scanning of the object or measuring its radiopacity with an industrial CT. In an alternative embodiment, a manufacturer may provide this information for dental implant products, and data tables may be available with radiopacity measurements of known materials. In an embodiment, these physical properties are stored in a database of object physical properties that may be accessed with the identification of the object. In alternative embodiments, one or more of the physical properties may be entered by a user input or image processing of one or more of the plurality of x-ray projection images may be used to derive the dimensions of the identified object.

At 112 a region of interest (ROI) is automatically located within the projection images by a processor analysis of the first plurality of x-ray projection images. The ROI may exemplary be automatically located to sufficiently constrain only the anatomical structures sought to be analyzed and any additional area required to provide context for the anatomical structures or to account for the identified artifact causing object. In some embodiments, it is desirable to locate the ROI at the center of the projection image. At 114 at least one dimension of an x-ray beam for a second plurality of x-ray projection images is calculated from the automatically located ROI. The at least one dimension of an x-ray beam is exemplarily at least a height and a width dimension of the x-ray beam required to image the ROI. In an exemplary embodiment, the at least one dimension of the x-ray beam is calculated based at least in part upon a 3D FOV to be reconstructed from the plurality of projection images.

At least one imaging parameter is adjusted at 116. In an embodiment, the imaging parameter is adjusted based upon the at least one identified object and the obtained a priori information. In exemplary embodiments, the at least one imaging parameter may include, but is not limited to, an x-ray beam intensity, an x-ray beam strength, at least one dimension of the x-ray beam, a number of projection images, a modification to the x-ray spectra of the x-ray beam, and dynamic filtering as described in further detail herein. In an exemplary embodiment, the a priori information of the at least one object obtained at 110 is a radiopacity of the at least one object. Based upon the radiopacity of the object, the imaging parameter of an intensity of the x-ray radiation beam can be adjusted in order to image the object in a manner that reduces the effect of any artifacts caused by the object, exemplarily a radiographic shadow cast by the object. In an exemplary embodiment, increasing the intensity of the x-ray radiation beam and/or modifying the x-ray spectra exposes the object to a greater amount of x-ray energy, more energy will pass through the object to be received by the receiver, mitigating the effect of the radiographic shadow. In still further embodiments, a number of projection images obtained in an imaging operation is adjusted based upon the a priori information of the identified at least one object.

At 118 the x-ray radiation beam is collimated in order to shape the x-ray radiation beam to the previously calculated at least one dimension of the x-ray beam for the second plurality of x-ray projection images. The x-ray radiation beam is filtered at 120 in order to attenuate by a portion of the x-ray radiation beam. Exemplarily, the filtering at 120 may be dynamic filtering in that portions of the x-ray beam receive different amounts of filtering such as to modify the x-ray strength across different portions of the x-ray radiation beam. In an exemplary embodiment, those portions of the x-ray radiation beam that are not directed at the artifact causing object are attenuated with the dynamic filtering for example to limit the radiation exposure of the patient while providing increased x-ray radiation to the artifact causing object in order to mitigate any resulting artifacts. A second plurality of x-ray projection images are obtained at 122 using the x-ray radiation beam as processed in a manner described above.

After the image acquisition sub method 102 has been completed, the image presentation sub method 104 may be performed as shown in FIG. 3B. It will be understood that, while the embodiments described above with respect to the image acquisition sub method 102 used one or more scout images as the first plurality of projection images, in an additional embodiment, the first plurality of projection images are acquired as a result of an imaging operation, and the second plurality of projection images are processed from the same acquired imaging data, only processed with the additional a priori information obtained as described above from the first plurality of projection images. Therefore, in some embodiments, the image presentation sub method 104 may present images acquired in other manners than those described above with respect to sub method 102. Similarly, the images acquired as described above with respect to sub method 102 may be presented in a manner other than those described with respect to sub method 104 and still remain within the scope of the present disclosure.

At 124, a 3D volume is reconstructed from the x-ray projection images. In embodiments, 3D reconstruction is performed exemplarily using an interactive reconstruction technique, e.g., an algebraic reconstruction technique (ART) that begins with an initial reconstruction and iteratively refines the reconstruction based upon additional information from the projection images. In additional embodiments, a non-interactive reconstruction technique, for example, filtered back projection (FBP) may be used.

The at least one object is identified at 126. In embodiments, the at least one object may be identified in the reconstructed 3D volume, or may be identified in the second plurality of projection images. The identification at 126 may exemplarily be dependent upon subsequent steps which may be performed as disclosed herein. At 128 at least a first object location of the identified object is determined and a second object location of the identified object is determined in the plurality of projection images. This identification of at least first and second object locations for the identified object can occur within the projection images of a single imaging operation, or may be determined in projection image or reconstructions from multiple imaging operations. Exemplarily, at 128 after the artifact causing object is identified in the plurality of projection images, a relative location for the object in each of the plurality of projection images is identified. At 130 the first object location is compared to the second object location in order to determine any differences in the location of the artifact causing object between different projection images of the plurality of projection images. From the comparison of the first object location to the second object location, an imaging error can be identified at 132. Exemplarily, large differences between the locations of the same artifact causing object between individual projection images of the plurality of projection images can be indicative of either a patient motion artifact due to the patient moving during the acquisition of the plurality of projection images. Additionally, such an identified difference in the first object location and the second object location may be indicative of a mis-calibration of the trace of the detector and/or the x-ray source. In one non-limiting example, an axis of rotation or the rotation path of the emitter and the detector about the object to be imaged may be identified as being mis-calibrated. Identification of these imaging errors at 132, may be used to initiate either corrective action, or a notification that such an error has been detected. Still further, since the geometrics of the identified object is known, location of the identified object can be simulated and the simulated location used as one of the first or second object locations while the actual object location is used as other of the first or second object locations. From a comparison of the first and second object locations, a distance and direction of movement from an expected position can be determined. This can enable correction for this movement.

In additional embodiments, the presentation of x-ray images can be facilitated with embodiments as disclosed herein, exemplarily by establishing a first coordinate system for a GUI configured to present medical images on a graphical display and a second coordinate system for the identified object at 134. In an embodiment, a priori information of the identified object maybe used in order to establish the second coordinate system. In an embodiment, the coordinate system includes a plurality of axes, exemplarily a three-axis, Cartesian system with x, y, and z axes. However, other coordinate systems can also be used, including but not limited to cylindrical, spherical, polar, or 2-axis Cartesian coordinates. In exemplary embodiments, the identified object may be in a 2D medical image from one or more of the acquired projection images, may be a 3D reconstructed volume from the plurality of x-ray projection images, or may be a 2D slice of the reconstructed 3D volume.

Optionally, at 136, the image comprising the identified object is transformed in order to align the first and second coordinate systems. The transformation may exemplarily include a rotation and/or a translation. The alignment of the first and second coordinate systems is achieved at least with respect to one of the axes of the first and second coordinate systems. Once the image is rotated to be in alignment with the GUI, the rotated image is presented in the GUI on a graphical display at 138 for observation or evaluation by a clinician.

Embodiments as disclosed herein may achieve advantages over imaging systems currently available in the art. Such advantages include improved image quality exemplarily by identification and correction of motion artifacts or attenuation of known sources of other reconstruction artifacts as disclosed herein. Additionally, some embodiments may achieve further advantages, for example, optimization of x-ray dose by controlling the dimensions of the x-ray beam in the imaging operation, controlling optimizing an x-ray beam intensity, through filtering of the x-rays to reduce areas of increased x-ray intensity exposure, or by optimizing an number of projection images in the imaging operation.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method of x-ray imaging, comprising:
   obtaining a priori information of at least one artifact causing object within a patient, wherein the a priori information includes a location of the at least one artifact causing object, and wherein the at least one artifact causing object comprises a dental implant;
   obtaining a plurality of x-ray projection images of the field of view; and
   reconstructing a three dimensional (3D) volume from the plurality of x-ray projection images of the field of view and the a priori information of the at least one artifact causing object to produce a reconstructed 3D image of the field of view.

2. The method of claim 1, wherein the a priori information comprises a physical property of the artifact causing object.

3. The method of claim 1, wherein the location of the artifact causing object is within a field of view to be imaged.

4. The method of claim 2, further comprising obtaining the physical property from an object database based upon the at least one identified object.

5. The method of claim 1, further comprising:
   prior to obtaining the plurality of x-ray projection images, obtaining an initial plurality of x-ray projection images of the patient;
   identifying at least one identified artifact causing object within the patient from the first plurality of x-ray projection images wherein the a priori information obtained is a priori information of the at least one identified artifact causing object; and
   adjusting at least one x-ray imaging parameter based upon the at least one artifact causing object and the obtained a priori information and obtaining the plurality of x-ray projection images according to the at least one adjusted x-ray imaging parameter.

6. The method of claim 5, further comprising deriving the location of the at least one identified artifact causing object from the initial plurality of x-ray projection images.

7. The method of claim 1, further comprising adjusting at least one x-ray imaging parameter used to obtain the plurality of x-ray projection images based upon the a priori information of at least one artifact causing object, wherein the at least one x-ray imaging parameter comprises at least one dimension of an x-ray beam used to obtain the plurality of x-ray projection images.

8. The method of claim 7, further comprising:
   automatically locating a Region of Interest (ROI) for the plurality of x-ray projection images from the a priori information of at least one artifact causing object within the patient; and
   determining the at least one dimension of the x-ray beam for the plurality of x-ray projection images from the located ROI.

9. The method of claim 1, further comprising receiving an identification of the at least one artifact causing object from a patient electronic medical record.

10. The method of claim 1 wherein the at least one x-ray imaging parameter is a strength of an x-ray beam used to acquire the plurality of x-ray projection images.

11. The method of claim 10, wherein the a priori information comprises radiopacity of the at least one artifact causing object.

12. The method of claim 1, further comprising:
    dynamically filtering an x-ray beam used to obtain the plurality of x-ray projection images to attenuate a portion of the x-ray beam out of alignment with the at least one artifact causing object.

13. The method of claim 12, wherein the location of the at least one artifact causing object is within a field of view to be imaged.

14. The method of claim 1, further comprising;
    identifying the at least one artifact causing object in the plurality of x-ray projection images based upon the a priori information of the at least one artifact causing object; and
    using the at least one artifact causing object in the plurality of x-ray projection images in reconstructing the 3D volume.

15. A system for x-ray imaging, the system comprising:
    an x-ray emitter configured to emit a cone beam of x-rays;
    a collimator operable to restrict at least one dimension of the cone beam of x-rays;
    an x-ray receiver configured to receive the x-rays to create projection images;
    a processor configured to obtain an identification of at least one artifact causing object, the at least one artifact causing object comprising a dental implant, and obtain a location of the dental implant;
    wherein the processor is further configured to receive a plurality of projection images from the x-ray receiver, reconstruct a three dimensional (3D) volume from the plurality of x-ray projection images and the identified dental implant and the location of the identified dental implant, and produce a reconstructed 3D image from the 3D volume; and
    a graphical display configured to present the reconstructed 3D image.

16. The system of claim 15, further comprising an object database that stores a plurality of artifact causing object physical properties, the processor receives at least one artifact causing object physical property corresponding to the identified at least one artifact causing object and uses the at least one physical property to reconstruct the 3D volume.

17. The system of claim 16, wherein the at least one artifact causing object physical property is radiopacity of the artifact causing object.

18. The system of claim 17, further comprising:
    an x-ray filter configured to attenuate at least a portion of the x-rays emitted from the emitter;
    wherein the processor is configured to operate the emitter to control a strength of the cone beam of x-rays emitted from the x-ray emitter based upon the radiopacity of the identified at least one artifact causing object; and
    wherein the processor is configured to operate the x-ray filter to attenuate a strength of a portion of the cone beam of x-rays based upon the position of the at least one artifact causing object.

19. The system of claim 15, wherein the processor further automatically locates a region of interest (ROI) about an object to be imaged based upon the obtained location of the dental implant and adjust the at least one dimension of the cone beam of x-rays based upon the ROI.

20. The system of claim 15, wherein the processor further adjusts a field of view about an object to be imaged based upon the obtained location of the at least one artifact causing object.

* * * * *